US011426545B2

(12) United States Patent
Miller et al.

(10) Patent No.: US 11,426,545 B2
(45) Date of Patent: Aug. 30, 2022

(54) HAND-HELD VAPORIZER DEVICE

(71) Applicant: Ghost Herbal Concepts Ltd, Tortola (VG)

(72) Inventors: Austen Charles Miller, Whitchurch (GB); Yann Glauser, London (GB)

(73) Assignee: The Green Labs Group, Inc., Los Angeles, CA (US)

( * ) Notice: Subject to any disclaimer, the term of this patent is extended or adjusted under 35 U.S.C. 154(b) by 358 days.

(21) Appl. No.: 16/340,072

(22) PCT Filed: Oct. 9, 2017

(86) PCT No.: PCT/GB2017/053049
§ 371 (c)(1),
(2) Date: Apr. 5, 2019

(87) PCT Pub. No.: WO2018/065793
PCT Pub. Date: Apr. 12, 2018

(65) Prior Publication Data
US 2020/0054072 A1 Feb. 20, 2020

(30) Foreign Application Priority Data

Oct. 7, 2016 (GB) .................................... 1617121
May 2, 2017 (GB) .................................... 1706948

(51) Int. Cl.
*A61M 15/06* (2006.01)
*A24F 40/46* (2020.01)
(Continued)

(52) U.S. Cl.
CPC ............. *A61M 15/06* (2013.01); *A24F 40/46* (2020.01); *A24F 40/485* (2020.01); *A24F 40/20* (2020.01); *H05B 3/141* (2013.01)

(58) Field of Classification Search
CPC ........ A24F 40/485; A24F 40/53; A24F 40/46; A24F 40/20
See application file for complete search history.

(56) References Cited

U.S. PATENT DOCUMENTS 9,532,603 B2 * 1/2017 Plojoux ................. A24F 40/485
2009/0293892 A1 12/2009 Williams et al.
(Continued)

FOREIGN PATENT DOCUMENTS

CN   204273249 U   4/2015
CN   105411004 A   3/2016
(Continued)

OTHER PUBLICATIONS

CN-201780075323.9 Chinese First Office Action of Chinese Patent Office dated Jan. 18, 2021.
(Continued)

*Primary Examiner* — Jean F Duverne
(74) *Attorney, Agent, or Firm* — Ashfields Law P.C.

(57) ABSTRACT

A vaporizer device is described in which a first air pathway extends from an inlet to a heating element. The heating element is configured to heat air from the first air pathway to produce heated air. A second air pathway extends from the heating element to a mouthpiece and is configured to carry the heated air. The first air pathway is configured to bring the air into thermal contact with at least one component in the second air pathway which absorbs heat from the heated air to heat air in the first air pathway and thereby reduce the energy needed to heat the air.

13 Claims, 6 Drawing Sheets

(51) Int. Cl.
*A24F 40/485* (2020.01)
*H05B 3/14* (2006.01)
*A24F 40/20* (2020.01)

(56) References Cited

U.S. PATENT DOCUMENTS

| | | |
|---|---|---|
| 2013/0247910 A1 | 9/2013 | Postma |
| 2014/0174383 A1 | 6/2014 | Kesten et al. |
| 2016/0211693 A1 | 7/2016 | Stevens et al. |
| 2016/0219938 A1* | 8/2016 | Mamoun ................ A24F 40/53 |
| 2016/0235124 A1 | 8/2016 | Krietzman |
| 2018/0317557 A1* | 11/2018 | Monsees ............... A61M 15/06 |

FOREIGN PATENT DOCUMENTS

| | | |
|---|---|---|
| EP | 3205220 A1 | 8/2017 |
| WO | 2006082571 A1 | 8/2006 |
| WO | 2012040512 A2 | 3/2012 |
| WO | 2013102609 A2 | 7/2013 |

OTHER PUBLICATIONS

EP-17784383.6 European first office action dated Feb. 10, 2021.
PCT/GB2017/053049 International search report and written opinion of international searching authority dated Jan. 17, 2018.

* cited by examiner

HAND-HELD VAPORIZER DEVICE

FIELD OF THE INVENTION

The present invention relates to improvements in hand-held vaporizer devices.

BACKGROUND OF THE INVENTION

A vaporizer is a device used to extract the active ingredients of a material, typically plant material such as herbs or herbal blends, for inhalation by a user. Vaporization involves heating the material to extract its active compounds as a vapour. In contrast, smoking involves the release of active compounds through combustion, typically with other particulate matter, noxious gasses and possible carcinogens. Interest in vaporizers for both recreational and medical use has increased recently, in part from the reduced risks compared to smoking.

In comparison to other drug delivery methods, such as ingestion, vaporization has a more rapid onset of pharmacological effect, direct delivery into the bloodstream via the lungs, and more precise titration such that the desired level is reached and not exceeded, enabling consistent and appropriate dosage.

Vaporizers utilizing convection-based heating methods employ the use of a heating element. Air is drawn into the vaporizer, heated by the heating element, and then passes across the material to extract its active ingredients as a vapour. The heated air and vaporized active ingredients are then delivered to the user via a mouthpiece. The air temperature needed to extract active ingredients from a herbal material varies depending on the herbal material, but generally ranges from 180 to 360° C.

In hand-help vaporizers, the energy needed to produce the required vapour temperature impacts usage time before the vaporizer's power source needs replenishing or recharging. Increasing the energy efficiency of hand-held vaporizers would increase the usage time for a given power source.

After the active ingredients are extracted from a herbal material by vaporization, the resulting vapour may be too hot to be comfortably and/or safely inhaled. U.S. Pat. No. 8,739,786 teaches the use of a conductive conduit to reduce the temperature of the vapour so it is safe and comfortable for inhalation by heat exchange with ambient air.

The presence of a heating element, air and vaporized active ingredients at temperatures of 180 to 360° C. in a hand-held vaporizer can result in parts of the vaporizer becoming hot. This may present risk of burning a user touching hot parts of the vaporizer, or at least make the vaporizer uncomfortable to hold, adversely affecting a user's experience of the vaporizer.

User experience of vaporizers is also impacted by the fluid resistance presented by the air flow path through the device. Users draw vapour from the vaporizers by applying suction to a mouthpiece to draw the vapour into their mouth. The resistance to the user's applied suction, also termed "resistance to draw" can impact a user's experience of the vaporizer.

SUMMARY OF THE INVENTION

In accordance with a first aspect of the invention, there is provided a vaporizer device comprising:
an inlet;
a first air pathway extending from the inlet to a heating element;
the heating element configured to heat air from the first air pathway to produce heated air;
a second air pathway extending from the heating element to a mouthpiece and configured to carry the heated air;
at least one component provided in the second air pathway absorbing heat from the heated air;
wherein the first air pathway is configured to bring the air into thermal contact with the at least one component.

Preferably, each at least one component comprises an inner surface and an outer surface, the inner surface defining a portion of the second air pathway, the outer surface defining a portion of the first air pathway.

Preferably, the at least one component comprises a receptacle for receiving a material to be used with the vaporizer device.

Preferably, the inner surface of the receptacle defines a cavity for receiving the material.

Preferably, the mouthpiece is provided at one end of the device and the inlet is provided adjacent the one end of the device.

Preferably, the at least one component comprises a heatsink configured to reduce a temperature of the heated air prior to entering the mouthpiece.

Preferably, the heatsink is provided at the inlet.

Preferably, the first air pathway surrounds the second air pathway.

Preferably, the first air pathway is configured as an insulating layer between the second air pathway and an outer case of the device.

In accordance with a second aspect of the invention, there is provided a vaporizer device comprising:
an inlet;
an air pathway extending from the inlet and configured in order to carry air to a heating element that heats the air, through a receptacle for receiving a material to be used with the vaporizer device, and to a mouthpiece;
a heatsink provided in the air pathway between the receptacle and the mouthpiece, a portion of the heatsink being provided adjacent the inlet;
wherein the heatsink is configured to absorb heat from the air carried from the receptacle to the mouthpiece and to simultaneously heat air entering the inlet.

Preferably, the heatsink comprises:
an end provided adjacent to the receptacle, the end having at least one aperture provided therein for the air to flow there through;
a side wall extending from the end, the side wall having an outer surface which is provided with a plurality of fins, wherein a portion of the outer surface is provided adjacent the inlet.

Preferably, the heatsink is provided adjacent the mouthpiece.

Preferably, the heatsink surrounds the mouthpiece.

Preferably, the heatsink is provided with an aperture formed therein to permit a portion of air entering the inlet to pass through the aperture and to the mouthpiece without being carried to the heating element.

Preferably, the aperture is configured such that the portion of air entering the inlet that passes through the aperture is between 30-50% of the air entering the inlet.

Preferably, the aperture is configured such that the portion of air entering the inlet that passes through the aperture is between 35-45% of the air entering the inlet.

Preferably, air flows into the inlet at a rate of 8-12 L/min in use, the aperture being configured such that 3.5-5 L/min of the air passes through the aperture.

In accordance with a third aspect of the invention, there is provided a heating device for a vaporizer device, comprising:

a first wall defining a conduit having a first end and a second end, the second end forming an outlet of the heating device;

a heating element provided in the conduit spaced from the first wall;

a plurality of further walls provided spaced from first wall, the further walls being interleaved to form a circuitous air pathway between an inlet of the heating device and the first end of the conduit.

Preferably, the plurality of further walls are configured substantially parallel to the first wall.

Preferably, the first wall has a flared portion at the second end.

Preferably, one of the further walls is formed integrally with the first wall, the one further wall extending from the second end of the first wall.

Preferably, the first wall and the further walls are formed from a low heat capacity material.

Preferably, the low heat capacity material is ceramic, stainless steel or aerogel.

Preferably, the first wall and the further walls define the circuitous air pathway with a cross-section that provides a predefined air flow rate.

Preferably, the air flow rate is in the range of 5-10 L/min.

Preferably, the air flow rate is in the range of 5-8 L/min.

In accordance with a fourth aspect of the invention, there is provided a vaporizer device comprising:

a mouthpiece comprising an elongate body having a distal end on which a user draws in use and a proximal end, an aperture extending from the distal end through the elongate body;

a portion of the elongate body adjacent the proximal end being received in the device to define a fluid passageway between the elongate body and the device;

the elongate body being slidably extendable out of the device, whereby a resistance to fluid flow through the fluid passageway changes as the elongate body is extended out of the device.

Preferably, the device further comprises a seal provided around the elongate body where the elongate body enters the device.

Preferably, the device further comprises a tube having a closed end and a side wall, an opening being provided in the side wall remote from the closed end, the portion of the elongate body being received in the tube, the fluid passageway being defined between the side wall of the tube and the elongate body.

Preferably, the side wall of the tube is tapered towards the closed end such that the fluid passageway gradually widens away from the closed end.

BRIEF DESCRIPTION OF THE FIGURES

The invention will now be described with reference to the accompanying drawings, in which.

DESCRIPTION OF PREFERRED EMBODIMENTS

Figure 1:
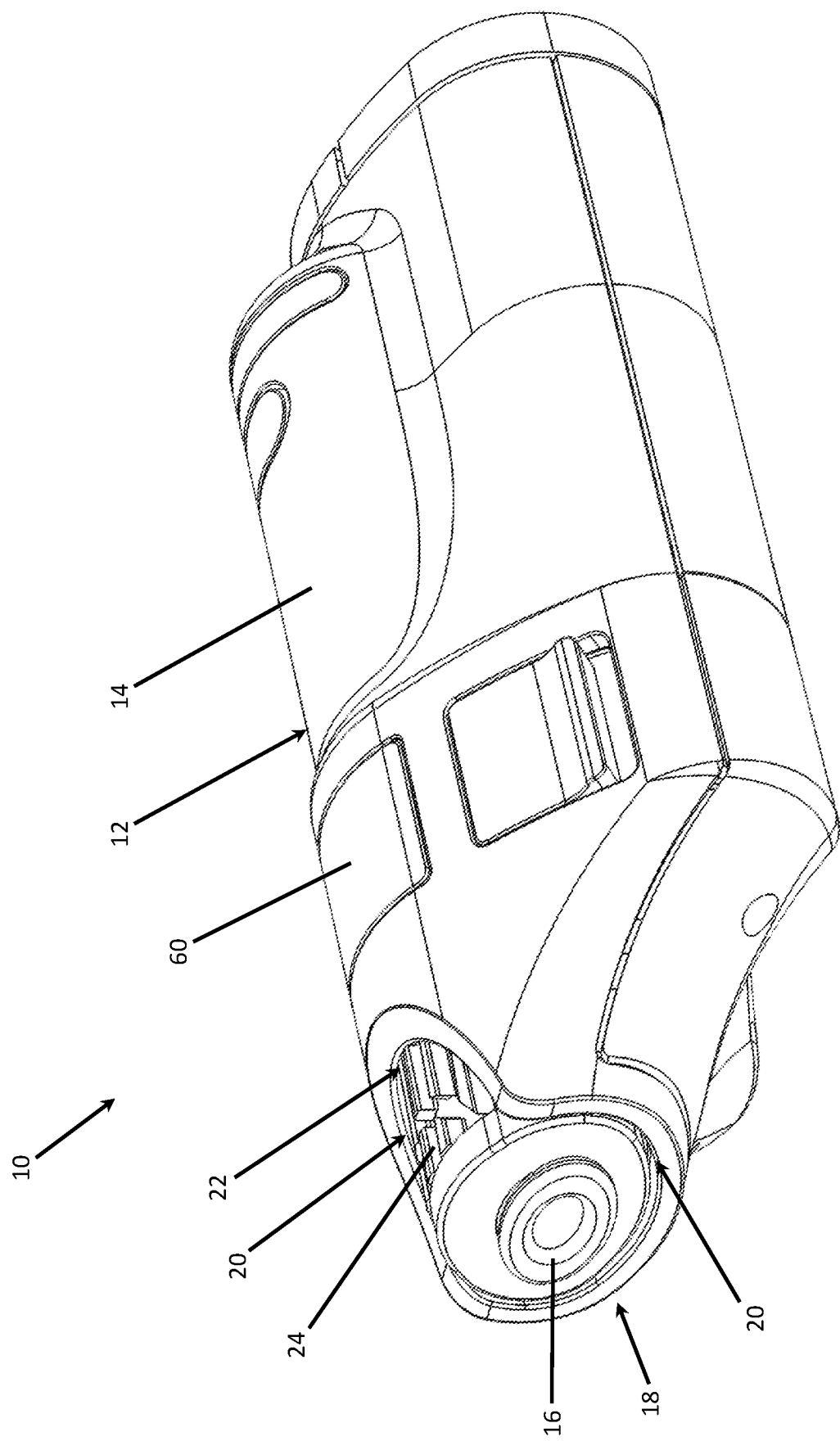
FIG. 1 is a perspective view of a vaporizer device according to an embodiment of the invention.

FIG. 1 shows a vaporizer device 10 having a body 12 with an outer case 14. The body 12 is of a size and shape to allow the vaporizer device 10 to be comfortably held in a user's hand. In use, air flows into the vaporizer device 10 and to a heating device. The vaporizer device 10 of the embodiment uses a convection-based heating element to heat the air, as will be described in detail below. Heated air flows from the heating element, across a material containing active ingredient(s) to extract the active ingredient(s) therefrom as a vapour, and the heated air and active ingredient(s) then exits the vaporizer device 10. Various materials containing active ingredients may be used with the vaporizer device 10, including but not limited to herbal materials and materials containing pharmaceutically active ingredients.

A mouthpiece 16 is provided at one end 18 of the body 12, from which heated air and active ingredient(s) exit the vaporizer device 10. A user may inhale on the mouthpiece 16 to receive the heated air and active ingredients.

The outer case 14 has an opening 20 therein adjacent the one end 18 of the body 12. The opening 20 defines an inlet 22 to the vaporizer device 10. Air is drawn into the vaporizer device 10 at the inlet 22 as the user inhales on the mouthpiece 16.

Depending on the material containing active ingredient(s) used with the vaporizer device 10, the temperature of the heated air required to extract the material's active ingredients may be too high for a user to comfortably inhale. The vaporizer device 10 includes a heatsink 24 that absorbs heat from the heated air and active ingredient(s) prior to entering the mouthpiece 18, cooling the air and active ingredient(s) inhaled by the user.

The inlet 22 is provided adjacent the heatsink 24. Locating the inlet 22 near the heatsink 24 allows air being drawn into the inlet 22 to be warmed by the heatsink 24. Warming air as it is drawn into the vaporizer device 10 reduces the energy required to heat the air to a temperature suitable for extracting active ingredient(s) from the material. Further, locating the inlet 22 at the heatsink 24 provides some forced convection to occur at the heatsink 24 when the user draws on mouthpiece 18, increasing the performance of the heatsink 24.

Figure 2:
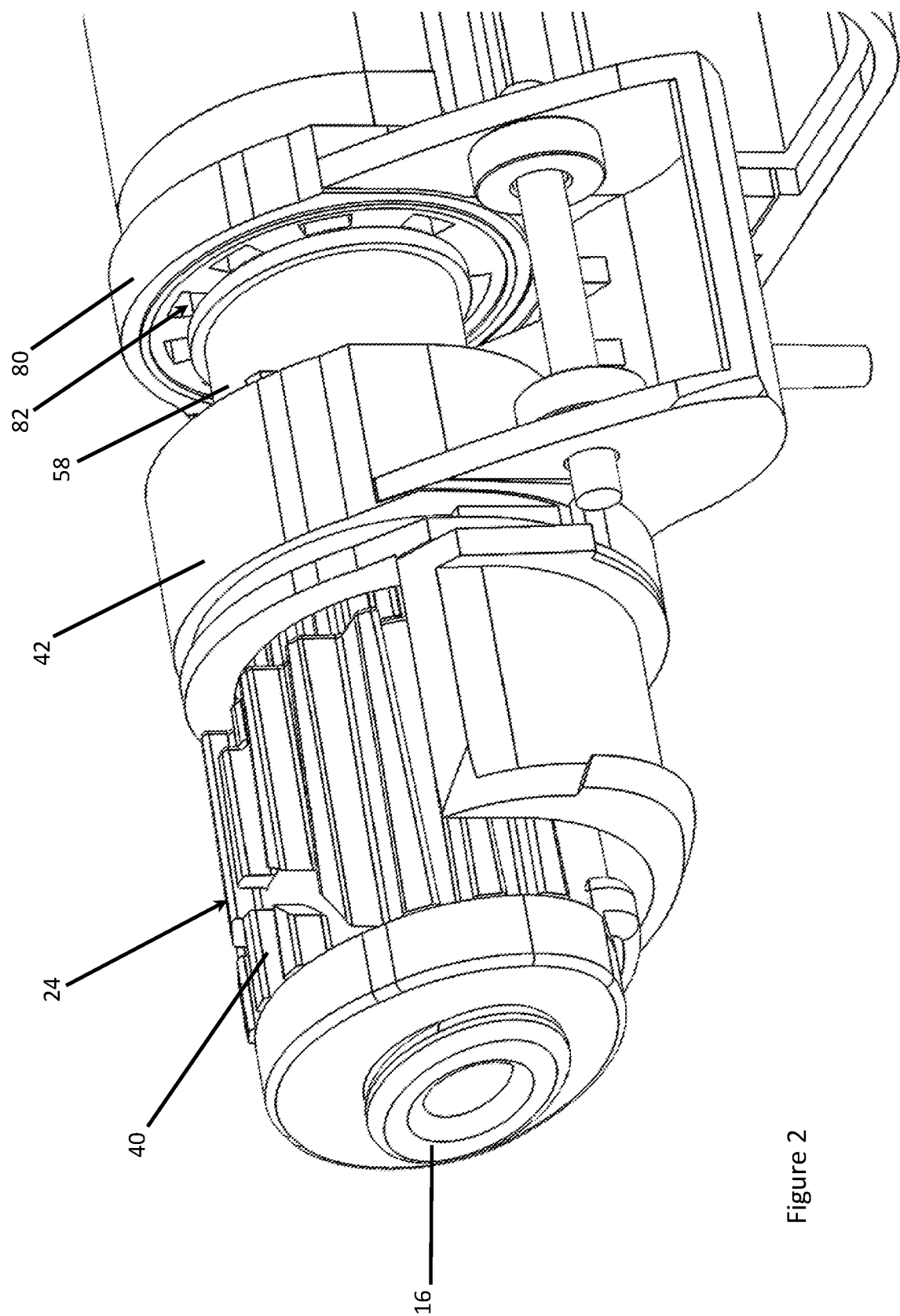
FIG. 2 is a partial perspective view of the vaporizer device of FIG. 1 with an outer case removed.

In the embodiment, the heatsink 24 is provided adjacent the one end 18 and surrounds the mouthpiece 16, as shown in FIG. 2. This is in contrast with vaporizer devices typical of the prior art in which the inlet and the mouthpiece are provided at opposed ends of the device in a manner akin to a cigarette. However, it has been found that providing the inlet and mouthpiece at the same end of the vaporizer device is beneficial as described herein.

Air drawn into the vaporizer device 10 at the inlet 22 enters an air pathway denoted generally at 28. The air pathway 28 of the embodiment consists of two sections: a first air pathway 30 extending from the inlet 22 to a heating element 32; and a second air pathway 34 extending from the heating element 32 to the mouthpiece 16. The first and second air pathways 30, 34 form a fluidly continuous path for passage of air through the vaporizer device 10 as described below.

The first air pathway 30 commences at the inlet 22, where the first air pathway 30 is defined by the heatsink 24. The heatsink 24 has a side wall 36 having an outer surface 38. A plurality of fins 40 are provided on the outer surface 38 of the heatsink 24. In other embodiments, pins or other suitable shapes may be substituted for the fins 40. In the vaporizer device 10 of the embodiment, the fins 40 are provided on the entire outer surface 38 to improve the heat exchange characteristics of the heatsink, however in other embodiments the fins 40 may be provided on a portion of the outer surface 38 in the region of the inlet 22.

The heatsink 24 is partially received within a first seal 42, with an end 44 of the heatsink 24 abutting the first seal 42 to form a fluid seal therewith. The first seal 42 includes a base 46 and a side wall 48. The base 46 has an inner surface 50, with which the end 44 of the heatsink 24 abuts, and an outer surface 52. The side wall 48 snugly mates with an outermost surface of the fins 40 such that channels 54 are formed between the fins 40, the outer surface 38 of the heatsink 24 and the side wall 48 of the first seal 42.

The channels 54 form part of the first air pathway 30, which continues via a plurality of apertures 56 formed through the first seal 42 that fluidly communicate with the channels 54.

The vaporizer device 10 includes a receptacle 58 into which material containing active ingredient(s) may be placed by the user. A door 60 is hinged to the body 12 to provide the user with access to the receptacle 58 in order to add material to or remove spent material from the receptacle 58. The door 60 has a flange 62 in which an opening 64 is formed. The receptacle 58 is received within the opening 64.

The receptacle 58 comprises a base 66 and a side wall 68 extending from the base 66. A plurality of apertures 78 are formed in the base 66 of the receptacle 58 to permit air flow into the receptacle 26 as described in more detail hereafter. Protrusions 70 extend outwardly from an end 72 of the side wall 68 remote from the base 66 of the receptacle 58. The protrusions 70 rest on a ledge 74 formed around the opening 64 to hold the receptacle 58 in place within the opening 64. The receptacle 58 is formed smaller than the opening 64 such that the side wall 68 is spaced from the flange 62 to form a gap 76 there between. The gap 76 surrounds the receptacle 58. In other embodiments, the flange 62 may be provided with protrusions and the receptacle 58 may have an outer lip which rests on the protrusions.

When the door 60 is in a closed position, the outer surface 52 of the first seal 42 sealingly engages with the receptacle 58 and the door flange 62. The apertures 56 in the first seal 42 are in fluid communication with the gap 76 between the receptacle 58 and the flange 62 to continue the first air pathway 30.

A second seal 80 is provided in the vaporizer device 10. When the door 60 is in a closed position, the second seal 80 sealingly engages with the door flange 62 and the receptacle base 66. The second seal 80 includes a plurality of outer apertures 82 in fluid communication with the gap 76 to continue the first air pathway 30. The outer apertures 82 extend through the second seal 80 and to a heating device 84 containing the heating element 32.

The first air pathway 30 continues into the heating device 84 and to the heating element 32 provided in the heating device 84, as will be described in detail hereafter. The heating element 32 heats the air flowing through the heating device 84, and the heated air exits the heating device 84 via an outlet 86 thereof and along the second air pathway 34.

The second seal 80 has an inner aperture 88 extending through the seal 80. The inner aperture 88 is shaped to match the outlet 86 of the heating device 84 such that when the heating device 84 abuts the second seal 80 a fluidly continuous path is formed there between. The second air pathway 34 carries heated air from the heating element 32 and continues from the outlet 86 and into the inner aperture 88.

Figure 3:
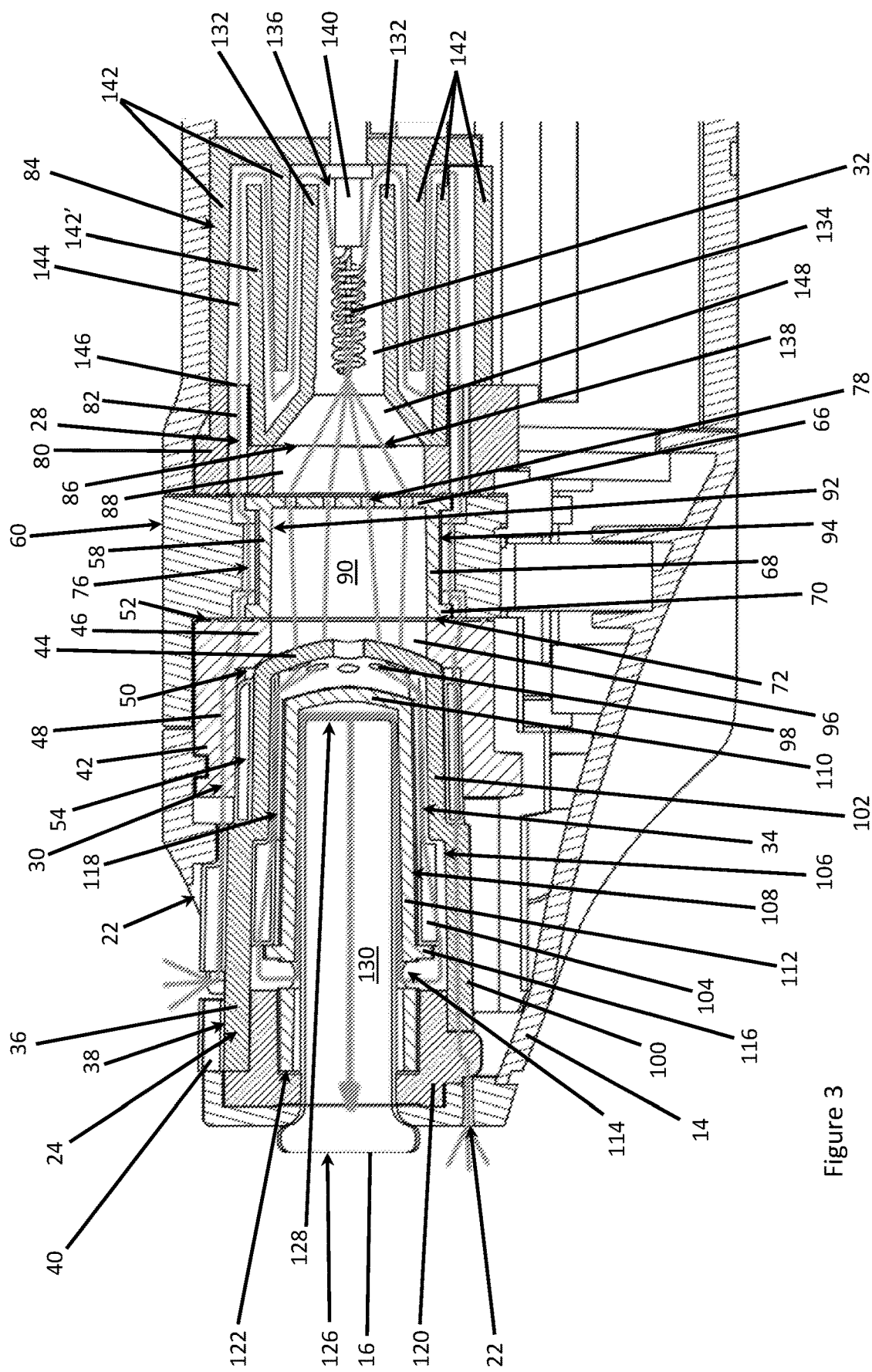
FIG. 3 is a partial cross section of the vaporizer device of FIG. 1.
Figure 4:
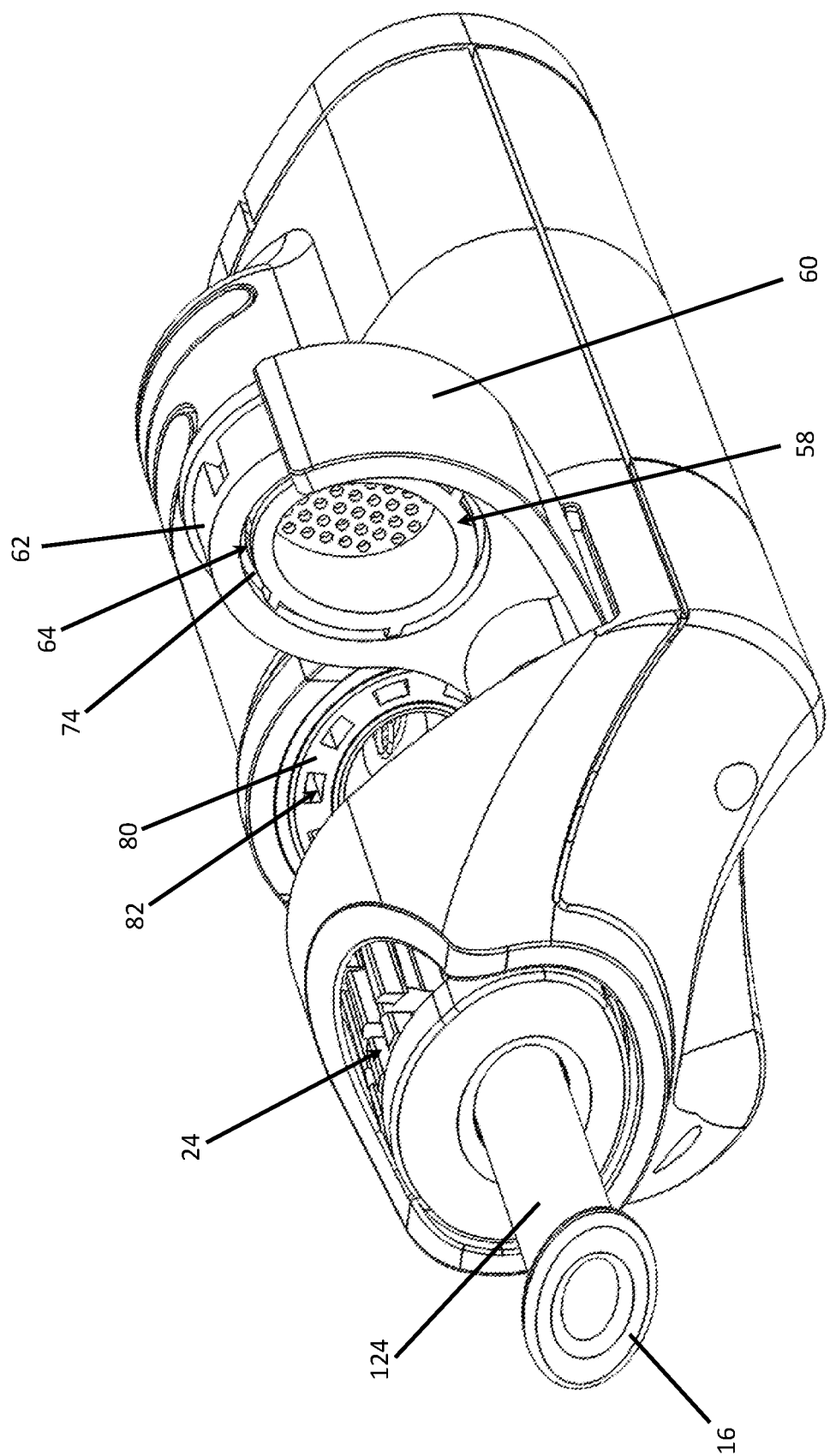
FIG. 4 is a perspective view of the vaporizer device of FIG. 1 with the door in an open position.

The inner aperture 88 is also aligned with the apertures 78 formed in the receptacle base 66, with the inner aperture 88 in fluid communication with the apertures 78. As shown in FIG. 3, the second seal 80 sealingly engages with the receptacle base 66. Part of this sealing engagement provided on the second seal 80 between the inner aperture 88 and the outer aperture 82 such that the first and second air pathways 30, 34 are separated.

The second air pathway 34 continues from the inner aperture 88 of the second seal 80, through the apertures 78 formed in the receptacle base 66 and into a cavity 90 formed in the receptacle 58. The cavity 90 has an inner surface 92. In use, the cavity 90 holds the material having active ingredients. Heated air that is carried along the second air pathway 34 enters the cavity 90 via the apertures 78 formed in the receptacle base 66 and is brought into contact with the material to release its active ingredients in vapour form. The cavity 90 forms part of the second air pathway 34.

Heated air in the cavity 90 also contacts the cavity's inner surface 92 with the result that the receptacle 58 absorbs some heat. Advantageously, an outer surface 94 of the receptacle 58 partly defines the gap 76 that forms part of the first air pathway 30. Air flowing along the first air pathway 30 will be brought into thermal contact with the receptacle's outer surface 94 and thereby be heated, reducing the energy required to heat the air to a desired temperature. Configuring the first air pathway 30 to bring the air flowing along it into thermal contact with the receptacle 58 provides some forced convection cooling of the receptacle 58 which, in turn, reduces the temperature of the device 10 in use.

In other embodiments, the receptacle 58 may be provided with a lid or cover (not shown) having apertures therein to permit airflow.

It is preferred that the receptacle 58 is formed from a low heat capacity material. This reduces the amount of energy the receptacle 58 will absorb from the heated air, in turn increasing the proportion of heat in the heated air used to extract active ingredients from the material in the cavity 90. One preferred low heat capacity material is a ceramic, however other suitable low heat capacity materials may be used, such as stainless steel.

The first seal 42 also has an inner aperture 96 formed in the base 46. The first seal 42's inner aperture 96 is configured to align and be in fluid communication with the cavity 90, as shown in FIG. 3, so that the second air pathway 34 continues along the inner aperture 96. As previously described, the end 44 of the heatsink 24 abuts the first seal's base 46 to form a fluid seal there between; this fluid seal separates the first and second air pathways 30, 34 by preventing air flowing along the channels 54 from passing into the inner aperture 96.

With the end 44 of the heatsink 24 abutting the base 46, the end 44 is exposed to heated air in the inner aperture 96. A plurality of apertures 98 are formed in the end 44 to allow heated air to pass through the end 44.

The heatsink 24 is generally U-shaped in the embodiment, as defined by the side wall 36 and the end 44. The side wall 36 has an outer section 100 remote from the end 44 and an inner section 102 adjacent the end 44. The inner section 102 is narrower than the outer section 100 so as to be received within the first seal 42. A plurality of inner fins 104 are formed on an inner surface 106 of the side wall 36. The inner fins 104 commence where the inner and outer sections 102, 100 meet and extend partially along the outer section 100.

A tube 108 having a closed end 110 and a side wall 112 is provided in the heatsink 24. The tube 108 has openings 114 formed in the side wall 112 spaced from the closed end 110. A lip 116 extends outwardly from the side wall 112 around the tube 108, adjacent the openings 114. When the tube 108 is received in the heatsink 24 the lip 116 rests on the inner fins 104 of the heatsink 24. In this position, the closed end 110 of the tube 108 is spaced from the end 24 of the heatsink 24.

The second air pathway 34 continues along a passageway 118 formed between the side wall 112 of the tube 108 and the side wall 36 of the heatsink 24. Heated air and vaporized active ingredients leaving the receptacle 58 pass through the apertures 98 in the end of the heatsink 24. The closed end 110 of the tube 108 forces the heated air and vaporized active ingredients along the passageway 118. The passageway 118 continues between the side walls 36, 112 of the heatsink 24 and tube 108, respectively, past the inner fins 104 of the heatsink 24 and into the openings 114 in the tube 108. This arrangement provides increased convective heat exchange between the heated air and vaporized active ingredients and the heatsink 24, cooling the heated air and vaporized active ingredients prior to inhalation by the user. As described above, the heatsink 24 also functions to warm air entering the inlet 22 and thereby reduce the energy required to heat the air to a desired temperature.

A third seal 120 is provided between the heatsink 24 and the tube 108 after the openings 114 to form a fluid seal therebetween and encourage the heated air and vaporized active ingredients into the openings 114. The third seal 120 extends around an open end 122 of the tube 108 to sealingly engage with the mouthpiece 16.

The mouthpiece 16 comprises an elongate body 124 having a distal end 126 on which a user draws in use and a proximal end 128, and an aperture 130 extending from the distal end 126 through the elongate body 124 to the proximal end 128. A portion of the elongate body adjacent the proximal end 128 is received in the tube 108. The passageway 118 continues from the openings 114, between the elongate body 124 and the side wall 112 of the tube 108, to the proximal end 128 of the elongate body where it is in fluid communication with the aperture 130.

The second air pathway 34 continues along the aperture 130, allowing heated air and vaporized active ingredients to exit the device 10 at the distal end 126 of the mouthpiece 16. The elongate body 124 may be slidably extendable out of the device 10 by a user.

As can be seen in FIG. 3, the second air pathway 34 generally extends along an axis A-A, with the first air pathway 30 being spaced from the axis A-A and generally surrounding the second air pathway 34. As seen in FIG. 2, the outer apertures 82 are spaced around the second seal 80 to surround the inner aperture 88. Although not shown in the drawings, the apertures 56 are similarly spaced around the first seal 42 so as to surround the inner aperture 96. The second air pathway 34 is carrying the heated air and vaporized active ingredients, so configuring the first air pathway 30 to generally surround the second air pathway 34 enables the first air pathway 30 to act as an insulating layer between the second air pathway 34 and the outer case 14 of the device 10, reducing the temperature of the device 10 in use. As described above, the first air pathway 30 is configured to bring the air therein into thermal contact with components in the second air pathway 34 that have absorbed heat, such as the receptacle 58 and the heatsink 24, reducing the energy required to heat the air to a desired temperature. This improves the energy efficiency of the device 10.

The heating device 84 of the embodiment, as shown in FIG. 3, comprises a first wall 132 defining a conduit 134 having a first end 136 and a second end 138. The second end 138 forms the outlet 86 of the heating device 84. The heating element 32 is provided in the conduit 134 spaced from the first wall 132 by a spacer 140. A plurality of further walls 142 are provided spaced from first wall 132. The further walls 142 are interleaved to form an air pathway 144 between an inlet 146 of the heating device 86 and the first end 136 of the conduit 134. The inlet 146 of the heating device 86 is in fluid communication with the outer apertures 82 formed in the second seal 80 so that the air pathway 144 forms part of the first air pathway 30.

The interleaved further walls 142 are positioned so that several further walls 142 are provided between the heating element 32 and the outer case 14 of the device 10. The interleaving of the further walls 142 results in the air pathway 144 of the heating device 86 having a circuitous, or zig-zag configuration. This places air in the air pathway 144 in thermal contact with each of the further walls 142, enabling heat exchange therewith.

In vaporizers typical of the prior art, a heating element is placed in contact with one of the walls of the device or with the receptacle so that the heating element must first heat the wall in order to heat the air. This arrangement increases the energy required in order to heat the air to the desired temperature since the heating element must also heat the thermal mass of the wall it is in contact with. In contrast, in the heating device 86, the heating element 32 is spaced from the walls 132, 142, with the result that the majority of the heat from the heating element 32 heats air in the conduit 134. Inevitably, some heat will be absorbed by the first wall 132 and further walls 142, however the circuitous nature of the air pathway 144 provides efficient heat exchange between the walls 132, 142 and air flowing through the air pathway 144. This heats air flowing in the air pathway 144 prior to entering the conduit 134, so that heat absorbed by the walls 132, 142 is recovered to the best extent possible. This configuration also reduces the extent to which the outer case 14 is heated by the heating element 32. In contrast, vaporizers typical of the prior art are known to get very hot in use and are often uncomfortable to hold.

The first wall 132 has a flared portion 148 adjacent its second end 138. The flared portion 148 commences after the heating element 32. In this manner, the heating element 32 substantially fills the conduit 134 to allow efficient heating of air flowing through past the heating element 32. The flared portion 148 ensures the outlet 86 corresponds with the size of the inner aperture 88. Beneficially, the flared portion 148 also creates some turbulence in the air flowing along the conduit 134 to increase homogeneity of the heated air temperature.

One of the further walls, shown in FIG. 3 as 142', is formed integrally with the first wall 132, the one further wall 142' extending from the second end 138 of the first wall 132. Thus the flared portion 148 also acts to space the further wall 142' sufficiently from the first wall 132 to allow another wall to be interleaved between them.

It is preferred that the first wall 132 and the further walls 142 are formed from a low heat capacity material to reduce the amount of energy the walls 132, 142 will absorb, which also increases the proportion of energy used by the heating element 32 that is used to heat air in the conduit 134. It is preferred that the low heat capacity material is a ceramic, however other suitable low heat capacity materials may be used such as stainless steel or aerogel. The number of and thickness of the further walls 142 may be altered according to the material from which the further walls 142 are formed, according to the material's heat capacity, strength and manufacturability characteristics. As described above, it is preferable for the total heat capacity of the first wall 132 and further wall 142 to be as low as practical.

In one arrangement, the further walls 142 may be formed from stainless steel, in which case the further walls 142 may be thinner than shown in the drawings. Such an arrangement may allow an increased number of further walls 142 to be provided in the heating device 84, which may improve heat exchange between the further walls 142 and air in the air pathway 144 and/or further reduce the extent to which the outer case 14 is heated by the heating element 32.

In some embodiments, the first wall 132 may be formed from a different material to the further walls 142. For instance, the further walls 142 are formed from stainless steel or another electrically conductive material. The first wall 132 may be formed from a material that is an electrical insulator to isolate the heating element 32 from the further walls 142.

Advantageously, the walls 132, 142 are configured to define the air pathway 144 with a cross-section that provides a predefined air flow rate when a user inhales on the mouthpiece 16. It has been found that an air flow rate in the range of 5-10 L/min enhances user experience of the device 10. Preferably, the air flow rate is in the range of 7-8 L/min.

Configuring the walls 132, 142 of the heating device 86 to act as an air flow restriction mechanism may assist control of the heating element 32, since a known rate of air flow is provided to the heating element 32. In one arrangement of the embodiment, an open-loop control arrangement may be used to provide energy to the heating element 32, for example by providing energy for a fixed time period. It should be appreciated that other control arrangements may also be used with the heating device 86, such as closed-loop control arrangements utilising one or more temperature sensors provided in the device 10. For example placement of such temperature sensors may be in the conduit 134, for instance in the flared portion 148.

In other embodiments, some or all of the flow rate control may be provided by the mouthpiece 16 and tube 108. The mouthpiece 16 and tube 108 may be shaped to provide the passageway 118 with a cross-sectional area that defines a desired air flow rate when a user inhales on the mouthpiece 16. One benefit of this arrangement is that it provides a degree of user-adjustable flow rate. As the user extends the elongate body 124 of the mouthpiece 16 out of the device 10, the length of the passageway 118 between the openings 114 and the proximal end 118 of the elongate body 124 shortens, reducing the air resistance provided by the passageway 118 and thus increasing the flow rate. Such an arrangement may permit a user to adjust the device 10's flow rate according to user preference. The side wall 112 of the tube 108 may be tapered towards the closed end 110 such that the passageway 118 gradually widens away from the closed end 110, which may allow for a wider range of flow rate to be controlled by the user. It is envisaged that flow rate control provided by the mouthpiece 16 and tube 108 may be combined with heating device flow rate control described above in some embodiments, for instance where the heating device flow rate control is used to provide an upper limit on the flow rate control afforded by the mouthpiece 16 and tube 108 to ensure the flow rate remains within a range where the heating element 32 is capable of heating air to a desired temperature.

Figure 5:
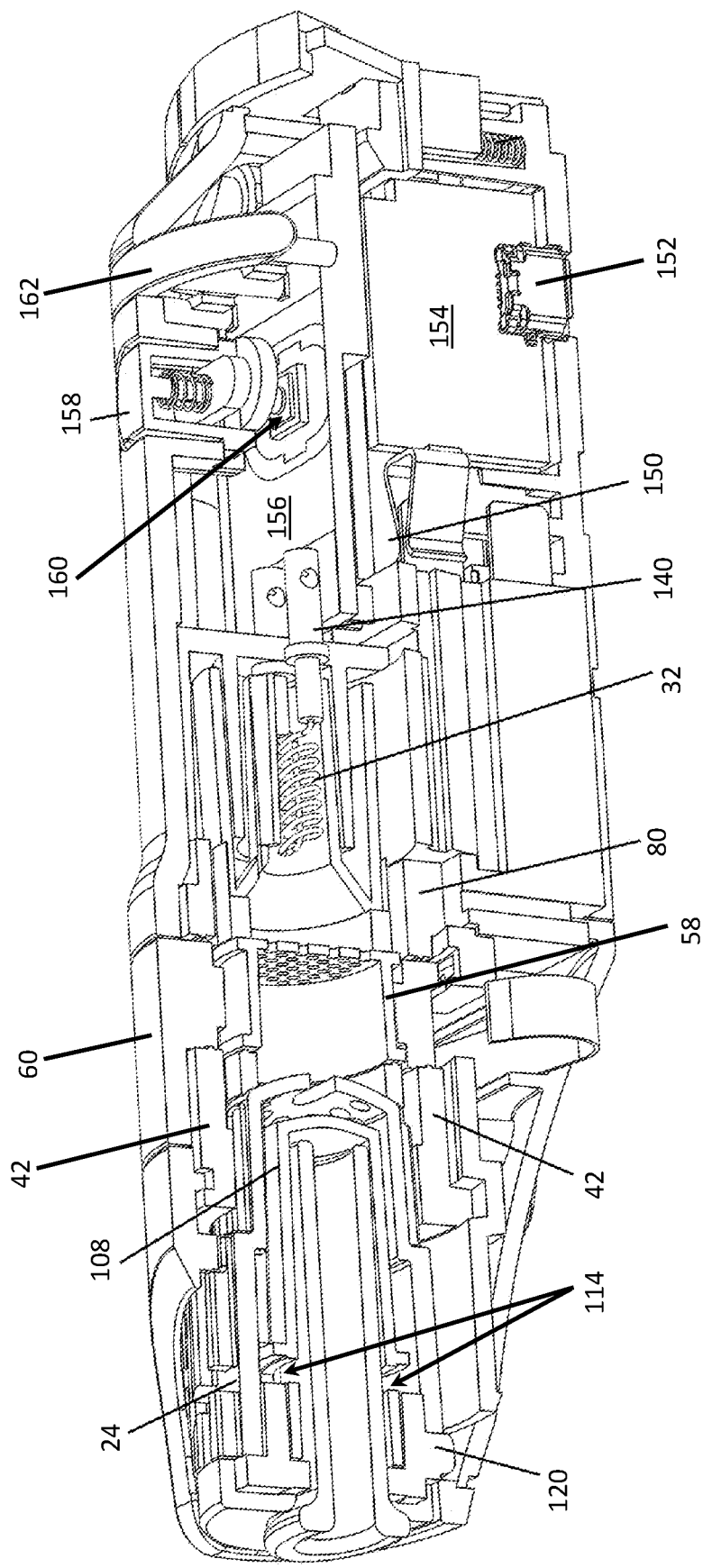
FIG. 5 is a side view, in partial cross section, of the vaporizer device of FIG. 1.

Referring now to FIG. 5, the vaporizer device 10 includes a power source which in the embodiment is a battery 150. Any battery technology with suitable power density may be used, with lithium-ion batteries preferred. The battery 150 may be recharged via a connector 152 which in the embodiment is a universal serial bus (USB) connector, more preferably a micro-USB connector. A battery charge circuit suitable to the battery type is provided on a first circuit board 154 to which the connector 152 is mounted. The battery 150 is removable from the vaporizer device 10 to allow a user to exchange batteries and continue using the vaporizer device 10 should the current battery be low on power.

The vaporizer device 10 further includes a second circuit board 156 on which any suitable control circuit for controlling the delivery of power to the heating element 32 may be provided. Such control circuits may be analogue or digital discrete circuit, and may include a microprocessor, an application specific integrated circuit ("ASIC"), embedded controller or other appropriate circuitry and may have memory or other data storage capabilities. Example control arrangements for delivering power to the heating element 32 have been described above, however other arrangements may also be used.

The user may provide control signals to the device 10 using a button 158 and associated switch 160. Indications may be provided to the user by means of a display 162 which in the embodiment may take the form of several light-emitting diodes (LEDs). The LEDs may be activated individually or together, may be configured to flash at one or more speeds or may be on continuously, and may each be a single colour or multi-colour, or combinations of these to provide a range of indications to the user. Such indications may include charge status of the battery 150, an 'on' state of the device 10, and whether the device 10 is ready for use.

To conserve energy, in the vaporizer device 10 of the embodiment power is only supplied to the heating element 32 in response to a signal indicating the user wishes to use the device 10. The signal may take any suitable form, including a control signal generated by the switch 160 in response to the user pressing the button 158. Alternatively, the signal may be provided from an airflow sensor provided at the inlet and configured to detect when a user begins to inhale on the mouthpiece. Beneficially, in these arrangements power is only supplied to the heating element 32 when the user is using the device 10. Since the user inhales in the mouthpiece 16 in use, air is drawn into the device at the inlet and flows along the first and second air pathways 30 and 34. The air flow results in forced convection at the heatsink, receptacle 58 and walls 132, 142 to coincide with the supply of power to the heating element 32.

Figure 6:
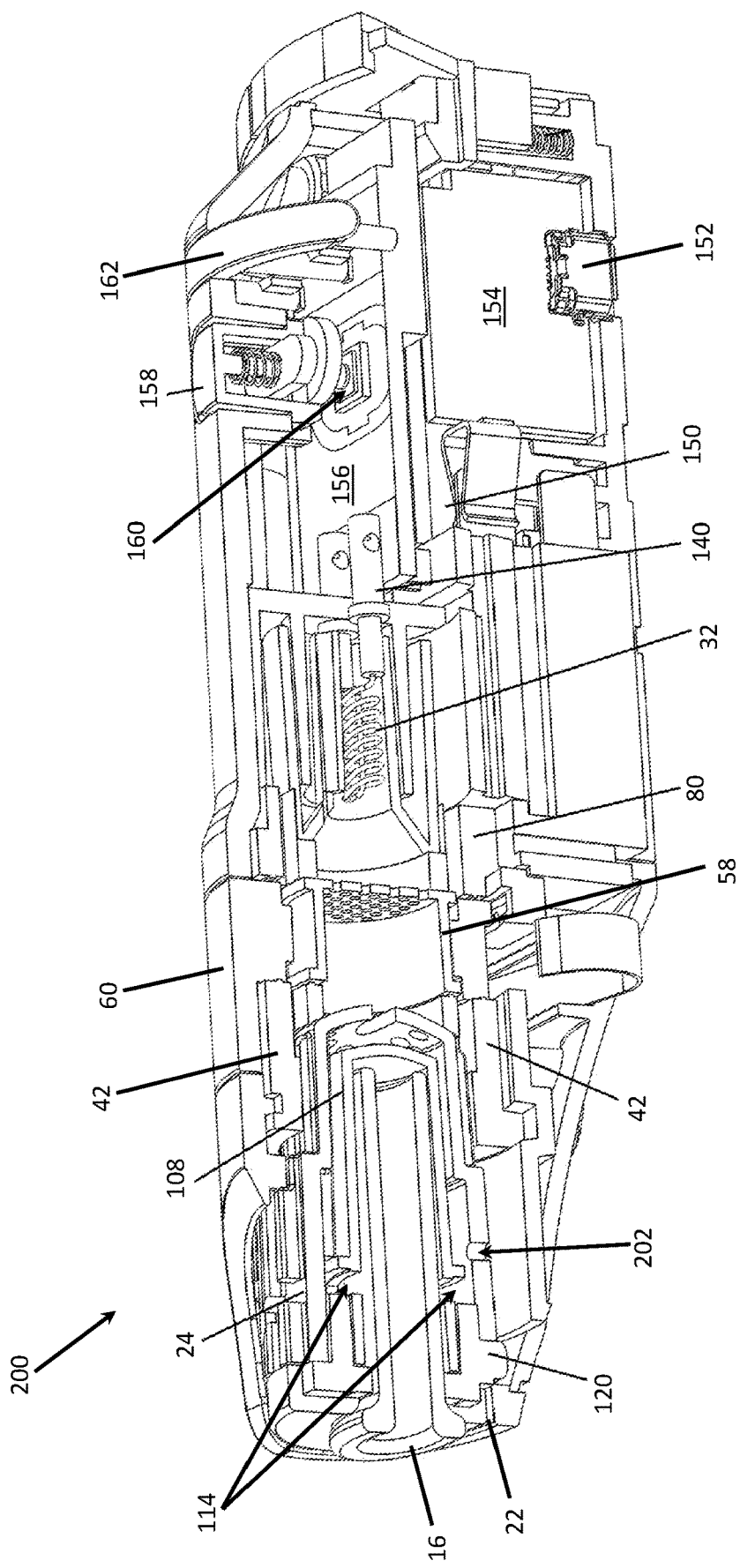
FIG. 6 is a side view, in partial cross section, of a vaporizer device according to another embodiment of the invention.

FIG. 6 shows a vaporizer device 200 according to a second embodiment of the invention. The vaporizer device 200 is of the same general form as the vaporizer device 10 of the first embodiment described above, and like reference numerals are used to denote like parts to those of the vaporizer device 10.

The vaporizer device 200 differs from the vaporizer device 10 in that the heatsink 24 of the vaporizer 200 has an aperture 202 formed therein to permit a portion of air entering the inlet 22 to pass through the aperture 202 and to the mouthpiece 16 without being carried to the heating element 32. Air passing through the aperture 202 mixes with heated air and vaporized active ingredients from the receptacle 58 as it passes into the mouthpiece 16, assisting in reducing the temperature of vapour inhaled by a user.

Advantageously, the aperture 202 further increases the energy efficiency of the vaporizer device 200. The portion of air entering the inlet 22 that passes through the aperture 202 is not heated by the heating element 32, reducing the energy used by the device 200.

The aperture 202 may be configured such that the portion of air entering the inlet that passes through the aperture is between 30-50% of the air entering the inlet, and preferably between 35-45% of the air entering the inlet. In the case of a vaporizer 200 in which 8-12 L/min enters the inlet 22 when a user draws on the mouthpiece 16, the aperture may be configured such that 3.5-5 L/min of the air passes through the aperture. Since less air is passes to the heating element 32, less energy is required by the device 200 per use to heat air to heat air to a desired temperature in order to extract active ingredients from the material in the receptacle 58. In addition, air flow through the aperture 202 may assist in cooling the heatsink 24, which in turn will increase the heat exchange between the heated air from the receptacle 58 and the heatsink 24, providing a further improvement in cooling of the heated air from the receptacle 58 prior to inhalation by a user, improving user experience.

Various embodiments disclosed herein are to be taken in the illustrative and explanatory sense, and should in no way be construed as limiting of the present invention as defined in the appended claims. It is to be understood that individual features shown or described for one embodiment may be combined with individual features shown or described for another embodiment.

All numerical terms, such as, but not limited to, "first", "second", "third", or any other ordinary and/or numerical terms, should also be taken only as identifiers, to assist the reader's understanding of the various embodiments, variations, components, and/or modifications of the present disclosure, and are not intended to create any limitations, particularly as to the order, or preference, of any embodiment, variation, component and/or modification relative to, or over, another embodiment, variation, component and/or modification.

The invention claimed is:

1. A vaporizer device comprising:
   an inlet;
   a first air pathway extending from the inlet and configured in order to carry air to a heating element that heats the air, through a receptacle for receiving a material to be used with the vaporizer device, and a second air pathway carrying the heated air to a mouthpiece; and
   a heatsink provided in the second air pathway between the receptacle and the mouthpiece, a portion of the heatsink being provided adjacent the inlet;
   wherein the heatsink is configured to absorb heat from the air carried from the receptacle to the mouthpiece and to simultaneously heat air entering the inlet,
   wherein the heatsink comprises an inner surface and an outer surface, the inner surface defining a portion of the second air pathway, the outer surface defining a portion of the first air pathway.

2. The vaporizer device of claim 1, wherein the heatsink comprises:
   an end provided adjacent to the receptacle, the end having at least one aperture provided therein for the air to flow there through; and
   a side wall extending from the end, the side wall having an outer surface which is provided with a plurality of fins, wherein a portion of the outer surface is provided adjacent the inlet.

3. The vaporizer device of claim 1, wherein the heatsink is provided adjacent the mouthpiece.

4. The vaporizer device of claim 3, wherein the heatsink surrounds the mouthpiece.

5. The vaporizer device of claim 1, wherein the heatsink is provided with an aperture formed therein to permit a portion of air entering the inlet to pass through the aperture and to the mouthpiece without being carried to the heating element.

6. The vaporizer device of claim 5, wherein the aperture is configured such that the portion of air entering the inlet that passes through the aperture is between 30-50% of the air entering the inlet.

7. The vaporizer device of claim 5, wherein air flows into the inlet at a rate of 8-12 L/min in use, the aperture being configured such that 3.5-5 L/min of the air passes through the aperture.

8. A heating device for a vaporizer device, comprising:
   a first wall defining a conduit having a first end and a second end, the second end forming an outlet of the heating device;
   a heating element provided in the conduit spaced from the first wall; and
   a plurality of further walls provided spaced from first wall, the further walls being interleaved to form a circuitous air pathway between an inlet of the heating device and the first end of the conduit, the air pathway passing between the plurality of interleaved further walls,
   wherein the first wall has a flared portion at the second end in the air pathway following the heating element.

9. The heating device of claim 8, wherein the plurality of further walls are configured substantially parallel to the first wall.

10. The heating device of claim 8, wherein one of the further walls is formed integrally with the first wall, the one further wall extending from the second end of the first wall.

11. The heating device of claim 8, wherein the first wall and the further walls are formed from a low heat capacity material.

12. The heating device of claim 8, wherein the first wall and the further walls define the circuitous air pathway with a cross-section that provides a predefined air flow rate.

13. The heating device of claim 12, wherein the air flow rate is in the range of 5-15 L/min.

* * * * *